United States Patent
Nitta et al.

(10) Patent No.: US 10,147,181 B2
(45) Date of Patent: Dec. 4, 2018

(54) IMAGE PROCESSING METHOD, IMAGE PROCESSING APPARATUS, X-RAY IMAGING APPARATUS, AND RECORDING MEDIUM STORING IMAGE PROCESSING PROGRAM

(71) Applicant: KONICA MINOLTA, INC., Chiyoda-ku (JP)

(72) Inventors: Kazuma Nitta, Suita (JP); Shinichi Horita, Osaka (JP)

(73) Assignee: Konica Minolta, Inc., Tokyo (JP)

(*) Notice: Subject to any disclaimer, the term of this patent is extended or adjusted under 35 U.S.C. 154(b) by 221 days.

(21) Appl. No.: 15/155,843

(22) Filed: May 16, 2016

(65) Prior Publication Data

US 2016/0343128 A1 Nov. 24, 2016

(30) Foreign Application Priority Data

May 21, 2015 (JP) ................................ 2015-103691

(51) Int. Cl.
| | |
|---|---|
| G06T 7/00 | (2017.01) |
| G06T 5/10 | (2006.01) |
| A61B 6/00 | (2006.01) |
| G01N 23/20 | (2018.01) |
| G06T 11/60 | (2006.01) |
| G06T 7/12 | (2017.01) |
| G06T 7/13 | (2017.01) |

(52) U.S. Cl.
CPC .......... *G06T 7/0012* (2013.01); *A61B 6/5211* (2013.01); *G01N 23/20* (2013.01); *G06T 5/10* (2013.01); *G06T 7/12* (2017.01); *G06T 7/13* (2017.01); *G06T 11/60* (2013.01); *G01N 23/20075* (2013.01); *G01N 2223/401* (2013.01); *G06T 2207/10116* (2013.01); *G06T 2207/20056* (2013.01)

(58) Field of Classification Search
CPC ......... G06T 7/00; G06T 7/0012; G06T 11/60; G06T 2207/10116; G01N 23/00; G01N 23/20; G01N 23/20075; G01N 2223/401; A61B 6/00; A61B 6/5211; A61B 6/484; G21K 2207/005
USPC ...................... 378/36, 62, 210; 382/128, 132
See application file for complete search history.

(56) References Cited

U.S. PATENT DOCUMENTS

| | | |
|---|---|---|
| 2013/0156284 A1 | 6/2013 | Koehler et al. |
| 2013/0279659 A1 | 10/2013 | Stampanoni et al. |
| 2014/0169522 A1 | 6/2014 | Hoshino |

(Continued)

FOREIGN PATENT DOCUMENTS

| | | |
|---|---|---|
| WO | WO 2014/092206 | 6/2014 |

OTHER PUBLICATIONS

Search Report dated Oct. 21, 2016 which issued in the corresponding European Patent Application No. 16169334.6.

(Continued)

*Primary Examiner* — Jurie Yun
(74) *Attorney, Agent, or Firm* — Cozen O'Connor

(57) ABSTRACT

An image processing method for generating a phase image includes generating a phase image on the basis of a differential image in a first direction based on image information of a subject and a differential image in a second direction different from the first direction, the second-direction differential image including information about a difference between signal values of pixels arranged side by side in the second direction in the first-direction differential image.

17 Claims, 10 Drawing Sheets

(56) References Cited

U.S. PATENT DOCUMENTS

2014/0177790 A1    6/2014  Bone et al.
2015/0131777 A1    5/2015  Makifuchi et al.

OTHER PUBLICATIONS

Schmid et al. "Evaluation of Interest Point Detectors", International Journal of Computer Vision 37(2), 151-172, 2000.

X DIRECTION

POSITION (C)
INTEGRAL REFERENCE COLUMN
POSITION (A)
INTEGRAL REFERENCE ROW
POSITION (B)
POSITION (D)
Y DIRECTION
X DIRECTION

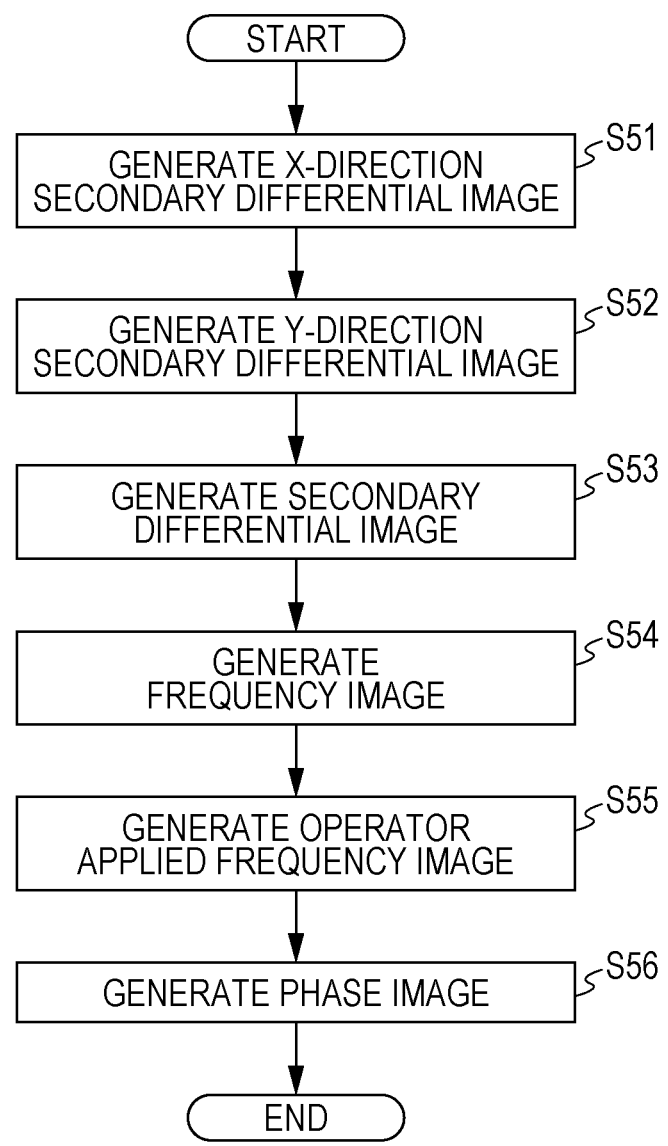

ized side by side
IMAGE PROCESSING METHOD, IMAGE PROCESSING APPARATUS, X-RAY IMAGING APPARATUS, AND RECORDING MEDIUM STORING IMAGE PROCESSING PROGRAM The entire disclosure of Japanese Patent Application No. 2015-103691 filed on May 21, 2015 including description, claims, drawings, and abstract are incorporated herein by reference in its entirety.

BACKGROUND OF THE INVENTION

Field of the Invention

The present invention relates to an image processing method, an image processing apparatus, an X-ray imaging apparatus, and a recording medium storing an image processing program.

Description of the Related Art

In recent years, aging is rapidly advancing in Japan. With the aging, the number of patients of osteoarthritis and articular rheumatism is also increasing. There is a magnetic resonance imaging (MRI) apparatus as a medical apparatus that appropriately understands conditions of the articular cartilage. However, the MRI apparatus is expensive, and imaging cost is thus also high. Further, since imaging time of the MRI apparatus is long, the load on a patient is large.

Thus, an X-ray imaging apparatus is used in image diagnosis for the above articular diseases. A common X-ray imaging apparatus captures an image of a subject on the basis of an X-ray absorption coefficient. Since the articular cartilage has a low X-ray absorption coefficient, the articular cartilage is less likely to be reflected on an X-ray image based on the absorption coefficient. On the other hand, since a bone part has a high X-ray absorption coefficient, the bone part is likely to be reflected on the X-ray image. Thus, in the X-ray image, a signal is interrupted in the boundary between bones. Thus, when a conventional X-ray imaging apparatus is used, the thickness of the articular cartilage is merely analogically understood through the distance between two bones adjacent to the articular cartilage (a part in which a signal is interrupted) in the X-ray image.

The application of a Talbot interferometer and a Talbot-Lau interferometer to a medical image is under consideration as a technique taking the place of such a conventional X-ray imaging apparatus.

The Talbot interferometer and the Talbot-Lau interferometer use a technique that does not acquire an X-ray image of a subject on the basis of an X-ray absorption coefficient as performed by a conventional X-ray imaging apparatus, but acquires a phase image of a subject on the basis of an X-ray phase change. The Talbot interferometer and the Talbot-Lau interferometer enable visualization of a living body soft tissue that cannot be read by a conventional X-ray imaging apparatus.

However, a differential phase image (hereinbelow, also referred to as "differential image") that can be obtained by the Talbot interferometer and the Talbot-Lau interferometer largely differs in view from an X-ray image of a common X-ray imaging apparatus, and is not familiar to doctors. Thus, image processing is performed on the differential image to make the differential image similar to an absorption image familiar to doctors. Examples of citations that disclose such image processing include US 2013/0156284 A, US 2013/0279659 A, and US 2014/0177790 A.

In US 2013/0156284 A, an optimization operation is used on a differential image to generate a phase image. In the optimization operation, an X-direction objective function is performed so that the gradient of a phase and a differential phase becomes minimum, and a Y-direction objective function is performed so that the sum of gradients with an upper or a lower pixel becomes minimum.

In US 2013/0279659 A, secondary-norm constrained optimization is used to generate a phase image. In the optimization operation, an X-direction objective function is determined by the secondary norm of the gradient of a phase and a differential phase, and a Y-direction objective function is reconfigured by optimization to which the secondary norm of the gradient with an upper or lower pixel value of a target pixel value is added.

The imaging apparatus disclosed in US 2014/0177790 A moves a two-dimensional grating in two directions to capture an image of a subject so that a phase image is reconfigured with respect to differential phase data holding information in the two directions.

When a diffraction grating is moved in one direction (X direction) to obtain a differential image as performed by the Talbot interferometer, the differential image includes only differential information in the direction in which the diffraction grating is moved, and includes no differential information in a direction other than the X direction. Thus, when the phase image is calculated on the basis of the differential image, many false images are included.

Regarding this point, in both the image processing of US 2013/0156284 A and the image processing of US 2013/0279659 A, the optimization is performed on the assumption that differential information in a direction different from the movement direction of the diffraction grating is continuous, and there is substantially no difference between signal values of pixels adjacent to a target pixel in the up-down direction (Y direction). Such an optimization operation merely calculates an average of differential values of pixels that are continuous in the up-down direction, and blurs the differential value on the image.

Further, the two-dimensional grating disclosed in US 2014/0177790 A makes the apparatus configuration, the imaging method, and the configuration of the grating itself more complicated than a one-dimensional grating. Thus, the cost becomes higher than an apparatus that uses a one-dimensional grating.

SUMMARY OF THE INVENTION

The present invention has been made in view of the above circumstances, and an object thereof is to provide an image processing method and an image processing apparatus that generate a phase image having a high accuracy in a simplified manner. Another object of the present invention is to provide an X-ray imaging apparatus that uses the image processing apparatus. Still another object of the present invention is to provide a recording medium storing an image processing program for causing a computer to execute the image processing method.

To achieve at least one of the abovementioned objects, according to an aspect, an image processing method for generating a phase image reflecting one aspect of the present invention comprises generating a phase image on the basis of a differential image in a first direction based on image information of a subject and a differential image in a second direction different from the first direction, the second-direction differential image including information about a difference between signal values of pixels arranged side by side in the second direction in the first-direction differential image.

To achieve at least one of the abovementioned objects, according to an aspect, an image processing apparatus reflecting one aspect of the present invention comprises a control processor for image processing, the control processor comprising a phase image generator configured to generate a phase image on the basis of a differential image in a first direction based on image information of a subject and a differential image in a second direction different from the first direction, the second-direction differential image including information about a difference between signal values of pixels arranged side by side in the second direction in the first-direction differential image.

To achieve at least one of the abovementioned objects, according to an aspect, an X-ray imaging apparatus reflecting one aspect of the present invention comprises: a light source configured to radiate X-rays; a Talbot interferometer or a Talbot-Lau interferometer including a one-dimensional grating; an imager configured to capture a moire image formed by the Talbot interferometer or the Talbot-Lau interferometer, the moire image including information about a subject by the X-rays; and an image processing apparatus configured to image-process the moire image, the image processing apparatus comprising a phase image generator configured to generate a phase image on the basis of a differential image in a first direction based on the moire image and a differential image in a second direction different from the first direction, the second-direction differential image including information about a difference between signal values of pixels arranged side by side in the second direction in the first-direction differential image.

To achieve at least one of the abovementioned objects, according to an aspect, a non-transitory computer-readable recording medium storing a program reflecting one aspect of the present invention causes a computer to execute an image processing method, the image processing method comprising generating a phase image on the basis of a differential image in a first direction based on image information of a subject and information about a difference between signal values of pixels arranged side by side in a second direction different from the first direction in the first-direction differential image.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 8 is a flow chart illustrating a process of processing a phase image using the Poisson's equation;

DESCRIPTION OF THE PREFERRED EMBODIMENTS

Hereinafter, an embodiment of the present invention will be described with reference to the drawings. However, the scope of the invention is not limited to the illustrated examples. Identical reference signs designate identical configurations throughout the drawings, and description thereof will be appropriately omitted.

<Phase Image Processing Apparatus>

Figure 1:
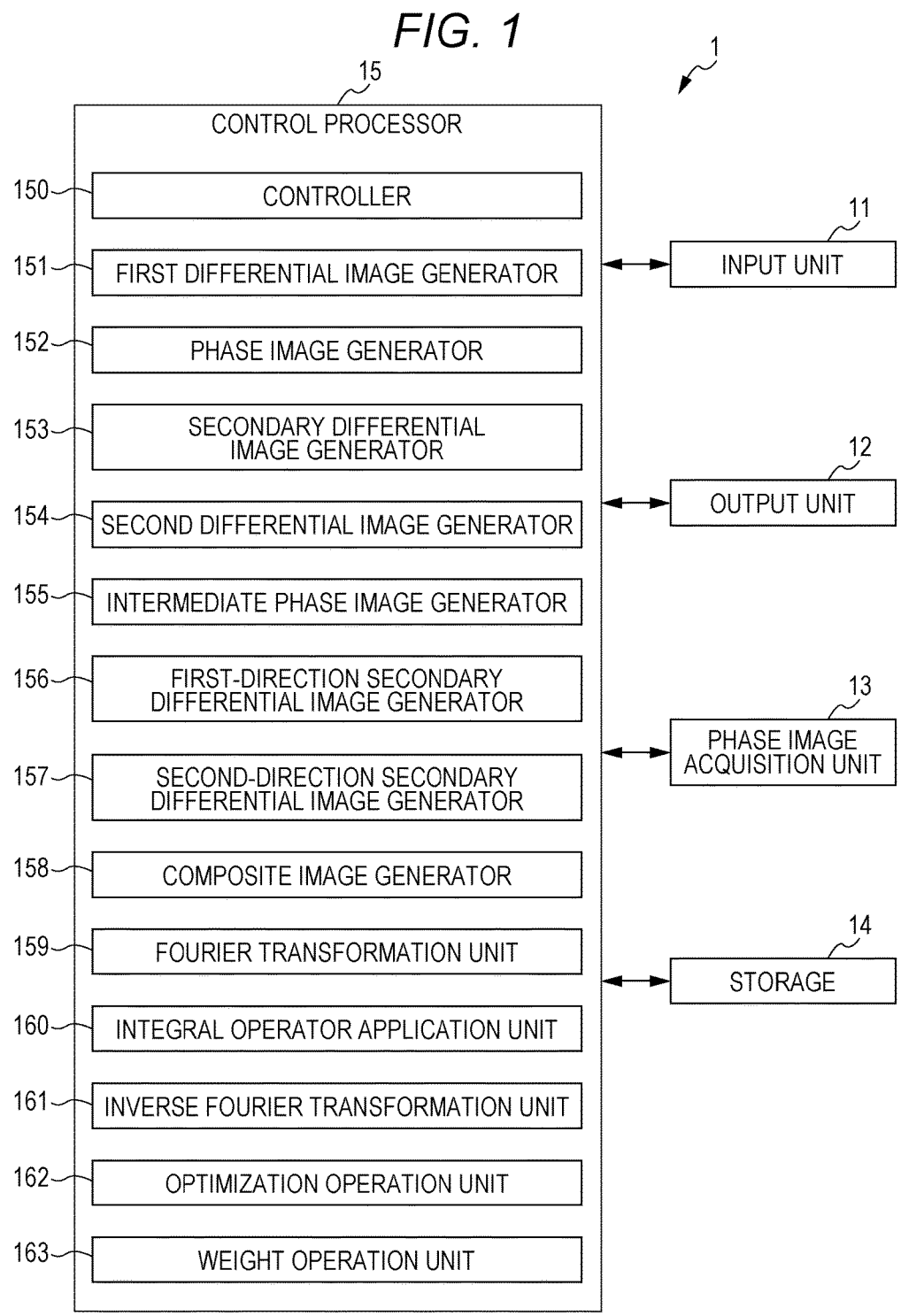
FIG. 1 is an explanatory diagram illustrating the configuration of a phase image processing apparatus of an embodiment of the present invention.

FIG. 1 is an explanatory diagram illustrating the configuration of a phase image processing apparatus. As illustrated in FIG. 1, the phase image processing apparatus 1 includes an input unit 11, an output unit 12, a phase image acquisition unit 13, a storage 14, and a control processor 15.

The input unit 11 is a device that is connected to the control processor 15 and inputs, for example, various commands such as a command instructing image processing using image information of a subject and various data required for image processing on image information of the subject to the phase image processing apparatus 1. The input unit 11 is, for example, a plurality of input switches to each of which a predetermined function is assigned, a key board, or a mouse.

The output unit 12 is a device that is connected to the control processor 15 and outputs commands or data input from the input unit 11 in accordance with control of the control processor 15. The output unit 12 is, for example, a display device such as a cathode ray tube (CRT), a liquid crystal display (LCD) or an organic EL display, or a printing device such as a printer. The output unit 12 displays image information of a subject, and various images such as a first-direction differential image, a secondary differential image, a second-direction differential image, and a phase image.

The input unit 11 and the output unit 12 may constitute a touch panel. In this case, the input unit 11 is a resistive film type or electrostatic capacitance type position input device which detects and inputs an operation position, and the output unit 12 is a display device. In this touch panel, the position input device is disposed on a display screen of the display device. When one or a plurality of inputtable input content candidates are displayed on the display device, and a user touches a display position that displays a desired input content, the position thereof is detected by a position input operation. A display content displayed on the detected position is input to the phase image processing apparatus 1 as an operation input content of the user. With such a touch panel, a user can easily intuitively understand an input operation. Thus, the phase image processing apparatus 1 that can be easily handled by a user is provided.

The phase image acquisition unit 13 is connected to the control processor 15 and acquires a phase image in accordance with control of the control processor 15. The phase image acquisition unit 13 may also serve as the input unit 11 or the output unit 12. The phase image acquisition unit 13 may be, for example, a circuit that performs wired or wireless data input/output with an external X-ray imaging apparatus, a communication IF unit, or an IF unit. The communication IF unit generates a communication signal which stores data to be transferred, the data being input from the control processor 15, in accordance with a communication protocol and transfers the generated communication signal to another region through a network. The communication IF unit may further include an interface circuit which performs data input/output with an external device using standard such as Bluetooth (registered trademark) standard, infrared data association (IrDA) standard, or universal serial bus (USB) standard. The IF unit is, for example, an RS-232C interface circuit of a serial communication method, an interface circuit using Bluetooth (registered trademark) standard, or an interface circuit using a USB standard. For example, the phase image acquisition unit 13 transmits a communication signal which stores an imaging condition or a control command to the X-ray imaging apparatus and receives image information from the X-ray imaging apparatus. Here, an image apparatus using a Talbot interferometer or a Talbot-Lau interferometer is suitably used as the X-ray imaging apparatus.

The storage 14 is a circuit that is connected to the control processor 15 and stores predetermined various programs and predetermined various data in accordance with control of the control processor 15. The predetermined various programs include, for example, an image processing program for generating a first-direction differential image on the basis of image information of a subject, an image processing program for generating a first-direction secondary differential image by further differentiating the first-direction differential image in the first direction, and an image processing program for generating an intermediate phase image by integrating the first-direction differential image in the first direction. The predetermined various data include, for example, imaging information by a radiology information system (RIS) or a hospital information system (HIS). Examples of the imaging information include patient information such as an identifier for specifying and identifying a patient (patient ID) or a patient name and imaging region (subject region) information which indicates a region of a living body being imaged.

The storage 14 stores an imaging condition obtained by associating a subject and an imaging condition suitable for imaging the subject, for example, in a table format. The storage 14 stores subject image information, and image information such as first-direction and second-direction differential images generated on the basis of the subject image information and a phase image generated on the basis of these differential images, a first-direction secondary differential image obtained by further differentiating the first-direction differential image in the first direction, and a second-direction secondary differential image obtained by further differentiating the second-direction differential image in the second direction in association with the imaging information.

The storage 14 includes, for example, a read only memory (ROM) which is a nonvolatile storage element and an electrically erasable programmable read only memory (EEPROM) which is a rewritable nonvolatile storage element. The storage 14 includes a random access memory (RAM) which stores data that is generated during the execution of the predetermined programs, that is, serves as a working memory of the control processor 15.

The control processor 15 is a circuit for controlling each unit of the phase image processing apparatus 1 according to the function of the unit to generate a phase image. The control processor 15 includes, for example, a central processing unit (CPU) and a peripheral circuit thereof. The control processor 15 generates various images such as a first-direction differential image, a secondary differential image, a second-direction differential image, a first-direction secondary differential image, and a second-direction secondary differential image in cooperation with the image processing programs stored in the storage 14.

The control processor 15 functionally includes a controller 150, a first differential image generator 151, a phase image generator 152, a secondary differential image generator 153, a second differential image generator 154, an intermediate phase image generator 155, a first-direction secondary differential image generator 156, a second-direction secondary differential image generator 157, a composite image generator 158, a Fourier transformation unit 159, an integral operator application unit 160, an inverse Fourier transformation unit 161, an optimization operation unit 162, and a weight operation unit 163 by the execution of the image processing programs.

The controller 150 is used for controlling each unit of the phase image processing apparatus 1 according to the function of the unit.

The first differential image generator 151 generates a differential image in the first direction on the basis of image information of a subject.

The phase image generator 152 generates a phase image on the basis of the first-direction differential image generated in the above and information about a difference between signal values of pixels arranged side by side in a second direction which is different from the first direction in the first-direction differential image. The information about the difference between signal values of pixels arranged side by side in the second direction is preferably a differential image in the second direction. The second-direction differential image is preferably generated in the second differential image generator (described below).

The secondary differential image generator 153 differentiates the first-direction differential image generated in the above in the second direction to generate a secondary differential image.

The second differential image generator 154 integrates the secondary differential image generated in the above in the first direction to generate a second-direction differential image, or differentiates an intermediate phase image (described below) in the second direction to generate a second-direction differential image, or specifies pixels each having a signal value that indicates an end of a subject in the first-direction differential image and decomposes a vector connecting the specified pixels into the first direction and the second direction to generate a second-direction differential image.

The intermediate phase image generator 155 integrates the first-direction differential image in the first direction to generate an intermediate phase image.

The first-direction secondary differential image generator 156 further differentiates the first-direction differential image in the first direction to generate a first-direction secondary differential image.

The second-direction secondary differential image generator 157 further differentiates the second-direction differential image in the second direction to generate a second-direction secondary differential image.

The composite image generator 158 adds the first-direction secondary differential image and the second-direction secondary differential image to generate a composite image.

The Fourier transformation unit 159 performs a Fourier transformation on the composite image to generate a frequency image.

The integral operator application unit 160 applies an integral operator to the frequency image to generate an integral operator applied frequency image.

The inverse Fourier transformation unit 161 performs an inverse Fourier transformation on the integral operator applied frequency image to generate a phase image.

The optimization operation unit 162 performs an optimization operation on a signal value of each pixel in the phase image using an objective function that includes a term of the second-direction differential image. The optimization operation unit 162 preferably performs an optimization operation using a weight calculated by the weight operation unit 163 (described below) in a coefficient of the term of the second-direction differential image.

The weight operation unit 163 calculates a weight that represents the continuity between signal values of pixels that are adjacent to each other in the second direction on the basis of the second-direction differential image. The calculated weight is used in the coefficient of the term of the second-direction differential image when the optimization operation is performed by the optimization operation unit 162.

<Phase Image Processing Method>

Figure 2:
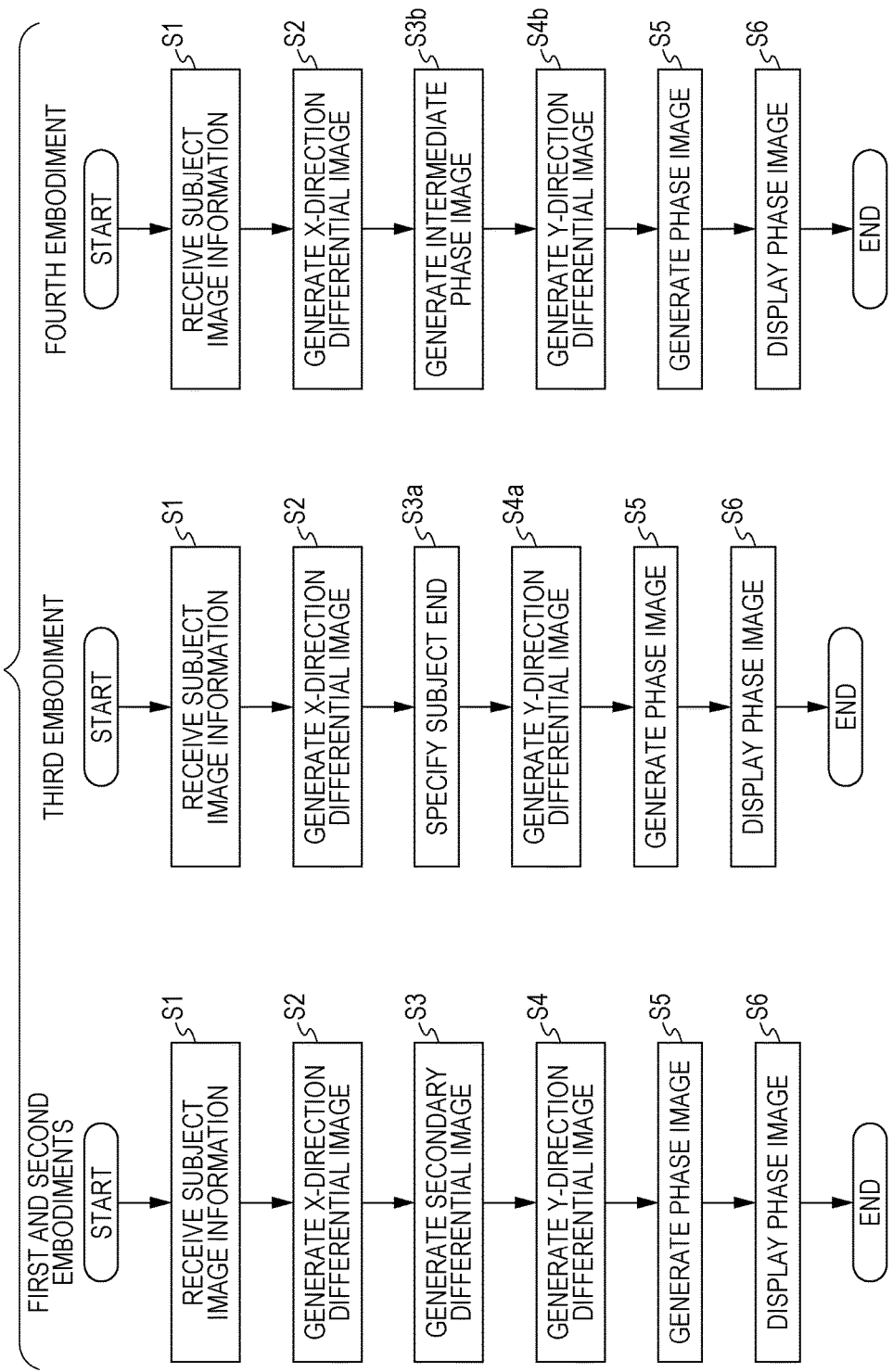
FIG. 2 is a flow chart illustrating steps of phase image processing according to first to fourth embodiments.

Phase image processing using the phase image processing apparatus 1 is executed in cooperation between the control processor 15 and various image processing programs stored in the storage 14. FIG. 2 is a flow chart illustrating steps of phase image processing methods according to first to fourth embodiments. The phase image processing method in the first embodiment includes a step (S1) of receiving image information of a subject obtained by, for example, an X-ray imaging apparatus, a step (S2) of generating a first-direction differential image on the basis of the image information of the subject, a step (S3) of differentiating the generated first-direction differential image in a direction (second direction) different from the first direction to generate a secondary differential image, a step (S4) of integrating the secondary differential image in the first direction to generate a second-direction differential image, a step (S5) of generating a phase image using the first-direction differential image and the second-direction differential image, and a step (S6) of displaying the generated phase image. The phase image processing method of the first embodiment uses the first differential image generator 151, the phase image generator 152, the secondary differential image generator 153, and the second differential image generator 154 in the control processor 15 illustrated in FIG. 1 to generate the phase image.

The phase image processing method of the second embodiment is the same as the method of the first embodiment except that the Poisson's equation is introduced into the step (S5) of generating a phase image. The phase image processing method of the second embodiment uses the first differential image generator 151, the phase image generator 152, the first-direction secondary differential image generator 156, the second-direction secondary differential image generator 157, the Fourier transformation unit 159, the integral operator application unit 160, and the inverse Fourier transformation unit 161 in the control processor 15 illustrated in FIG. 1 to generate the phase image. The phase image processing method of the third embodiment is the same as the method of the first embodiment except that a step of specifying an end of a subject is performed instead of the step of generating a secondary differential image in the first embodiment and a Y-direction differential image is generated on the basis of information about the end of the object. The phase image processing method of the third embodiment uses the same configuration of the control processor as the first embodiment to generate a phase image. The phase image processing method of the fourth embodiment is the same as the method of the first embodiment except that a step of generating an intermediate phase image is performed instead of the step of generating a secondary differential image in the first embodiment and a Y-direction differential image is generated using the intermediate phase image. The phase image processing method of the fourth embodiment uses the first differential image generator 151, the phase image generator 152, the intermediate phase image generator 155, and the second differential image generator 154 in the control processor 15 illustrated in FIG. 1 to generate a phase image. Hereinbelow, the phase image processing method of each of the embodiments will be described.

<First Embodiment: Phase Image Processing Method>

(Step S1: Reception of Image Information of Subject)

First, the phase image acquisition unit 13 receives image information of a subject from, for example, the X-ray imaging apparatus (S1). The image information of the subject is two-dimensional data including at least information about an edge (end) of the subject. The edge of the subject indicates a pixel that is adjacent to a pixel having a signal value indicating that no subject is present and has a signal value indicating that the subject is present. The image information received by the phase image acquisition unit 13 is preferably image information of the subject obtained by a Talbot interferometer or a Talbot-Lau interferometer. The reason thereof will be described below in a sixth embodiment.

(Step S2: Generation of X-direction Differential Image)

Figure 3:
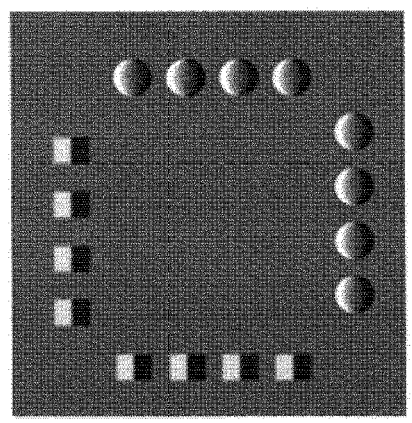
FIG. 3 is an example of a first-direction differential image of a subject generated on the basis of image information of the subject.

Next, the first differential image generator 151 differentiates the above subject image information in a first direction to generate a first-direction differential image (S2). FIG. 3 is an example of the X-direction differential image generated in step S2. In the following description, a direction of differentiating image information in a two-dimensional image is defined as an X direction, and a direction perpendicular to the X direction is defined as a Y direction. As illustrated in FIG. 3, the first-direction (X-direction) differential image is an image with light-shade contrast reflected according to the degree of inclination of an X-ray wave surface by the subject as well as two-dimensional data that can render a soft tissue (for example, a cartilage part) with a higher definition than an X-ray absorption image. The X-direction differential image is represented by the following formula (1).

[Formula 1]

$$dphX(u, v) \tag{1}$$

In the above formula (1), ph(u, v) represents a signal value of a pixel whose X coordinate is located at u and Y coordinate is located at v in the subject image information, and dphX(u, v) represents a signal value of a pixel that is located at coordinates (u, v) in the X-direction differential image.

The first-direction differential image includes differential information in the first direction (X direction) and includes substantially no differential information in a direction different from the first direction. Here, "including substantially no differential information" does not mean "including completely no differential information in a direction different from the first direction", but means that, for example, even when the first-direction differential image is integrated in the second direction, correct information in the second direction cannot be obtained.

(Step S3: Generation of Secondary Differential Image)

Figure 4:
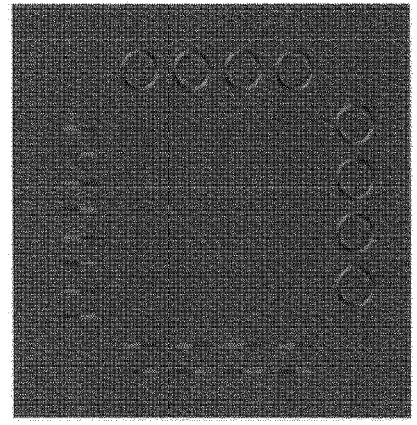
FIG. 4 is an example of a secondary differential image generated by differentiating the X-direction differential image in a Y direction.

Next, the secondary differential image generator 153 differentiates the X-direction differential image obtained in the above in the Y direction to generate a secondary differential image (S3). The differentiation in the Y direction is performed by calculating a difference between a signal value of a pixel that is located at coordinates (u, v) in the X-direction differential image and a signal value of a pixel that is located at coordinates (u, v−1) and adjacent to the above pixel on the negative side in the Y direction or a pixel that is located at coordinates (u, v+1) and adjacent to the above pixel on the positive side in the Y direction. FIG. 4 is the secondary differential image generated in step S3. The secondary differential image is represented by the following formula (2).

[Formula 2]

$$\frac{d(dphX(u, v))}{dy} = dphX(u, v) - dphX(u, v \pm 1) \quad (2)$$

The secondary differential image is a two-dimensional image obtained by differentiating the X-direction differential image in the Y direction to extract a part of Y-direction differential information in the subject image information.

(Step S4: Generation of Y-direction Differential Image)

Figure 5:
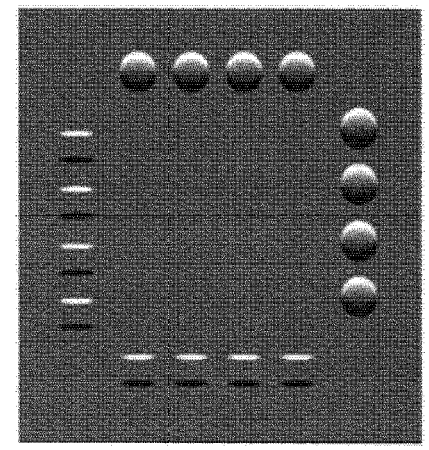
FIG. 5 is an example of a Y-direction differential image generated by integrating the secondary differential image in the X direction.

The second differential image generator 154 integrates the secondary differential image obtained in the above in the X direction to generate a Y-direction differential image (S4). FIG. 5 is the Y-direction differential image generated by the integration in the X direction.

Figure 6:
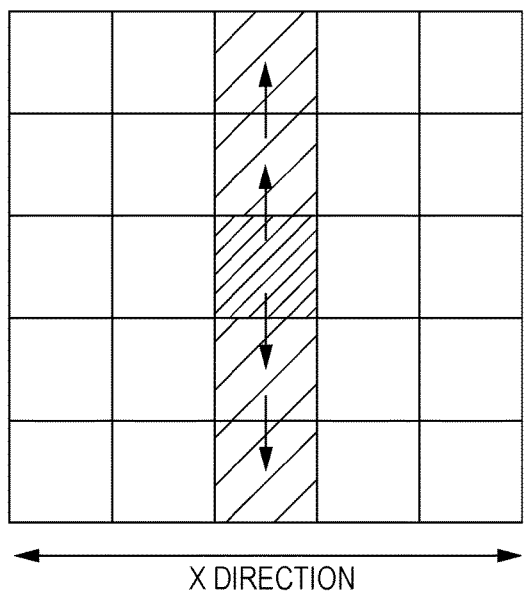
FIG. 6 is a diagram describing a method for integrating a secondary differential image in the X direction.

A method of the X-direction integration and a method for determining an integral constant in step S4 will be specifically described with reference to FIG. 6. FIG. 6 is a diagram describing the X-direction integration method in step S4. FIG. 6 illustrates a secondary differential image in a 5×5 pixel region as an example. However, the number of pixels included in the pixel region is not limited thereto, and one or more integration target ranges including the entire or apart of the secondary differential image can be set.

As illustrated in FIG. 6, the integration in step S4 first calculates the sum of changes in signal values of pixels arranged side by side in the up-down direction (Y direction) in the secondary differential image for each of the first to fifth columns. Then, a column having the smallest sum of changes in signal values of pixels is set as a reference column. In FIG. 6, the third column is set as the reference column for convenience' sake. The sum total of changes in signal values of pixels in the reference column (the third column in FIG. 6) is defined as the integral constant. The integral constant is represented by formula (3). The integral constant is the sum total obtained by calculating a difference between a signal value of a pixel that is located at coordinates (u, v) and a signal value of a pixel that is located at coordinates (u, v−1) and adjacent to the above pixel on the negative side in the Y direction or a pixel that is located at coordinates (u, v+1) and adjacent to the above pixel on the positive side in the Y direction for each of the pixels including the above pixel arranged side by side in the Y direction and adding up the calculated differences.

[Formula 3]

$$\min = \Sigma(dphX(u, v) - dphX(u, v \pm 1)) \quad (3)$$

Next, integration represented by the following formula (4) is performed on signal values of pixels that are located on the positive side in the X direction with respect to the reference column (the fourth column and the fifth column in FIG. 6).

[Formula 4]

$$\text{out}(u, v) = \text{out}(u-1, v) + dphX(u, v) \quad (4)$$

In formula (4), out(u, v) represents a signal value of a pixel that is located at coordinates (u, v) in the Y-direction differential image. When the integration of formula (4) is applied, the signal value of the pixel located at coordinates (u, v) in the Y-direction differential image is calculated by the sum of a signal value of a pixel located at coordinates (u, v) in the X-direction differential image and a signal value of a pixel located at coordinates (u−1, v) in the Y-direction differential image.

On the other hand, integration represented by the following formula (5) is performed on signal values of pixels that are located on the negative side in the X direction with respect to the reference column (the first column and the second column in FIG. 6).

[Formula 5]

$$\text{out}(u, v) = \text{out}(u+1, v) - dphX(u+1, v) \quad (5)$$

In formula (5), out(u, v) represents a signal value of a pixel that is located at coordinates (u, v) in the Y-direction differential image. When the integration of formula (5) is applied, the signal value of the pixel located at coordinates (u, v) in the Y-direction differential image is calculated by the difference between a signal value of a pixel located at coordinates (u+1, v) in the Y-direction differential image and a signal value of a pixel located at coordinates (u+1, v) in the X-direction differential image.

In this manner, the second differential image generator 154 integrates the secondary differential image in the X direction to generate a Y-direction differential image. The Y-direction differential image generated in this manner is generated on the basis of the X-direction differential image, and thus includes Y-direction differential information of the coefficient of X in the subject image information.

(Step S5: Generation of Phase Image)

Figure 7:
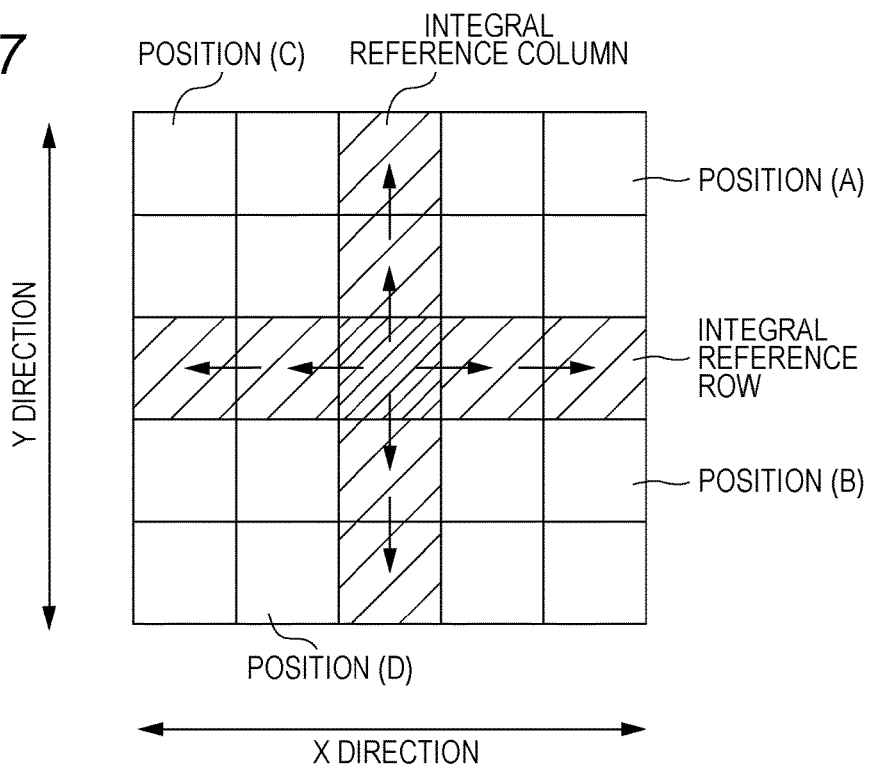
FIG. 7 is a diagram describing a process of generating a phase image.

The phase image generator 152 generates a phase image using the X-direction differential image and the Y-direction differential image obtained in the above (S5). A process of generating the phase image in step S5 will be specifically described with reference to FIG. 7. FIG. 7 is a diagram describing the process of generating the phase image in step S5. First, a reference row in the X direction is set on the X-direction differential image in the same manner as the setting of the reference column in step S4 except for a difference in the directions of the row and the column.

Specifically, as illustrated in FIG. 7, the sum of changes in signal values of pixels that are arranged side by side in each row (X direction) in the X-direction differential image is calculated for each of the rows, and a row having the smallest sum of changes in signal values of pixels is set as a reference row (integral reference row) in the X direction. In FIG. 7, the third row is set as the integral reference row for convenience' sake. The sum of changes in signal values of pixels in the integral reference row is defined as an X-direction integral constant.

Similarly, a reference column (integral reference column) in the Y direction is set on the Y-direction differential image in the same manner as the setting of the reference column in step S4. Then, the sum of changes in signal values of pixels in the integral reference column is defined as a Y-direction integral constant.

Then, all pixels in the X-direction differential image are integrated using the following formulae (6) to (9) according to positions (A) to (D) of the pixels with respect to the integral reference row and the integral reference column defined in the above.

(A) The integration is performed using formula (6) on a pixel that is located on the positive side in the X direction with respect to the integral reference column as well as on the positive side in the Y direction with respect to the integral reference row.

[Formula 6]

$$\text{value\_}X = \text{out}(u-1, v) + dphX(u, v)$$

$$\text{value\_}Y = \text{out}(u, v-1) + dphY(u, v) \quad (6)$$

In the above formula (6), value_X is the X-direction integral constant, value_Y is the Y-direction integral constant, and out (u, v) is a signal value of a pixel located at coordinates (u, v) in the phase image.

Then, value_X and value_Y calculated in formula (6) are substituted into formula (7) to calculate a signal value at coordinates (u, v) in the phase image.

[Formula 7]

$$\text{out}(u, v) = \frac{\text{value\_}X + yWeight \times \text{value\_}Y}{1.0 + yWeight} \quad (7)$$

In formula (7), since the Y-direction differential image do not perfectly reproduce Y-direction image information of the subject, the Y-direction differential image is not used as the phase image as it is, but a weight (yWeight) which is set by a user in any manner within the range of 0.0 to 1.0 is multiplied by the Y-direction differential image to be used. That is, yWeight in formula (7) is a value that is set by a user in any manner within the range of 0.0 to 1.0.

(B) The integration is performed using formula (8) on a pixel that is located on the positive side in the X direction with respect to the integral reference column as well as on the negative side in the Y direction with respect to the integral reference row.

[Formula 8]

$$\text{value\_}X = \text{out}(u-1, v) + dphX(u, v)$$

$$\text{value\_}Y = \text{out}(u, v+1) - dphY(u, v+1) \quad (8)$$

Then, value_X and value_Y calculated in formula (8) are substituted into formula (7) to calculate a signal value at coordinates (u, v) in the phase image.

(C) The integration is performed using formula (9) on a pixel that is located on the negative side in the X direction with respect to the integral reference column as well as on the positive side in the Y direction with respect to the integral reference row.

[Formula 9]

$$\text{value\_}X = \text{out}(u+1, v) - dphX(u+1, v)$$

$$\text{value\_}Y = \text{out}(u, v-1) + dphY(u, v) \quad (9)$$

Then, value_X and value_Y calculated in formula (9) are substituted into formula (7) to calculate a signal value at coordinates (u, v) in the phase image.

(D) The integration is performed using formula (10) on a pixel that is located on the negative side in the X direction with respect to the integral reference column as well as on the negative side in the Y direction with respect to the integral reference row.

[Formula 10]

$$\text{value\_}X = \text{out}(u+1, v) - dphX(u+1, v)$$

$$\text{value\_}Y = \text{out}(u, v+1) - dphY(u, v+1) \quad (10)$$

Then, value_X and value_Y calculated in formula (10) are substituted into formula (7) to calculate a signal value at coordinates (u, v) in the phase image.

The phase image generated in the above manner includes information about the Y-direction differential image and thus has a higher accuracy than a phase image that is generated by processing only information about the X-direction differential image.

(Step S6: Display of Phase Image)

The controller 150 displays the phase image generated in step S5 on the output unit 12.

<Second Embodiment: Phase Image Processing Method>

The present embodiment is the same as the first embodiment except that the Poisson's equation is used to generate a phase image in step S5 of the first embodiment. Hereinbelow, step S5 which is modified from the first embodiment will be described. Since the other steps are the same as those of the first embodiment, description thereof will be omitted.

The Poisson's equation is a second-order partial differential equation represented by the following formula (11) when f=f(x1, x2, x3, . . . xn) is a known function, and u=u(x1, x2, x3, . . . xn) is an unknown function.

[Formula 11]

$$\frac{d^2}{dx_1^2}u(x_1,\ldots,x_n) + \frac{d^2}{dx_2^2}u(x_1,\ldots,x_n) + \ldots \frac{d^2}{dx_n^2}u(x_1,\ldots,x_n) = \quad (11)$$

$$f(x_1,\ldots,x_n)$$

(Step S5: Generation of Phase Image)

FIG. 8 is a flow chart illustrating a process of generating a phase image using the Poisson's equation. In order to apply the Poisson's equation, the first-direction secondary differential image generator 156 further differentiates the X-direction differential image obtained in step S2 of the first embodiment in the X direction to generate an X-direction secondary differential image (S51). The X-direction secondary differential image is represented by the following formula (12).

[Formula 12]

$$\frac{d}{dx} dphX(u, v) \qquad (12)$$

Further, the second-direction secondary differential image generator 157 further differentiates the Y-direction differential image obtained in step S4 of the first embodiment in the Y direction to generate a Y-direction secondary differential image (S52). The Y-direction secondary differential image is represented by the following formula (13).

[Formula 13]

$$\frac{d}{dy} dphY(u, v) \qquad (13)$$

Next, the composite image generator 158 adds the X-direction secondary differential image represented by the above formula (12) and the Y-direction secondary differential image represented by the above formula (13) to generate a composite image (S53). The composite image is represented by the following formula (14).

[Formula 14]

$$\frac{d^2}{dx^2 dy^2} ph(u, v) = \frac{d}{dx} dphX(u, v) + \frac{d}{dy} dphY(u, v) \qquad (14)$$

The Fourier transformation unit 159 performs a Fourier transformation on the composite image represented by formula (14) to transform the composite image into a frequency image (S54). The frequency image is represented by the following formula (15). In formula (15), $d_{kn}$ is a coefficient represented by the following formula (16).

[Formula 15]

$$\frac{d^2}{dx^2 dy^2} ph(u, v) = \sum_{k=1}^{L} \sum_{n=1}^{L} d_{kn} \sin\left(\frac{\pi k u}{L}\right) \sin\left(\frac{\pi n v}{L}\right) \qquad (15)$$

[Formula 16]

$$d_{kn} = \frac{1}{L^2} \int_0^{2L} \int_0^{2L} \frac{\partial g(u, v)}{\partial x} \sin\left(\frac{\pi k u}{L}\right) \sin\left(\frac{\pi n v}{L}\right) dxdy \qquad (16)$$

The integral operator application unit 160 applies a modified second-order integral operator to the frequency image to perform second-order integration to generate an operator applied frequency image (S55). The inverse Fourier transformation unit 161 performs an inverse Fourier transformation on the operator applied frequency image to generate a phase image (S56). The phase image is represented by the following formula (17). In formula (17), an amplitude is regarded as zero, and a DC component is ignored (k=n=0).

[Formula 17]

$$ph(u, v) = -\left(\frac{L}{\pi}\right)^2 \sum_{k=1}^{L} \sum_{n=1}^{L} \frac{d_{kn}}{(k^2 + \lambda n^2)} \sin\left(\frac{\pi k u}{L}\right) \sin\left(\frac{\pi n v}{L}\right) \qquad (17)$$

As described above, the application of the Poisson's equation to a composite image obtained by adding an X-direction secondary differential image and a Y-direction secondary differential image enables the generation of a phase image including Y-direction information. The phase image generated in this manner has a higher accuracy than a phase image generated using only an X-direction differential image.

<Third Embodiment: Phase Image Processing Method>

The present embodiment is the same as the first embodiment except that, as illustrated in FIG. 2, a step (step S3a) of specifying an end (edge) of a subject in an X-direction differential image and a step (step S4a) of extracting a Y component of a vector connecting the edge to generate a Y-direction differential image are included instead of steps S3 and S4 of the first embodiment. Hereinbelow, steps S3a and S4a which are modified from the first embodiment will be described. Since the other steps are the same as those of the first embodiment, description thereof will be omitted.

(Step S3a: Specification of End of Subject)

Figure 9A:
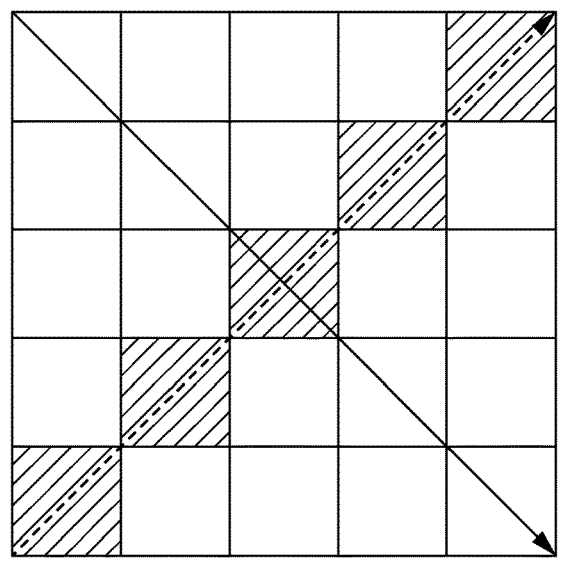
FIG. 9A is an example of a measurement pixel region.
Figure 9B:
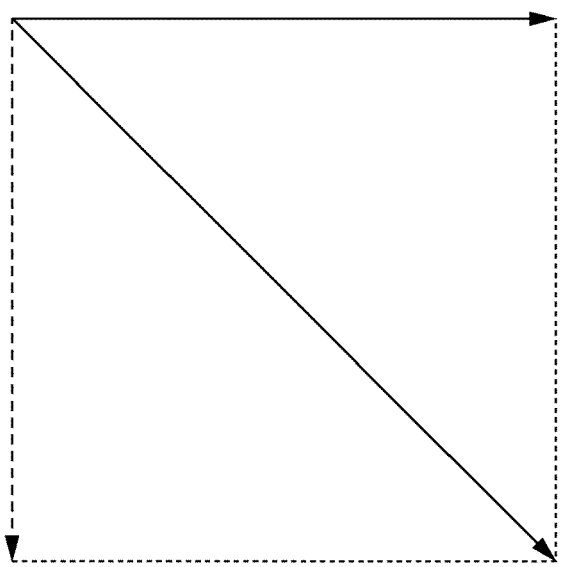
FIG. 9B is a diagram describing a method for decomposing a vector component into the X direction and the Y direction to extract a Y component.

A method for specifying an end (edge) of a subject in an X-direction differential image will be described with reference to FIGS. 9A and 9B. First, the controller 150 sets any one pixel in the X-direction differential image as a target pixel and sets a measurement pixel region of, for example, 5×5 having the target pixel on the center. FIG. 9A is an example of the measurement pixel region. The center pixel in the measurement pixel region of FIG. 9A is the target pixel. The measurement pixel region of FIG. 9A is merely an example, and the measurement pixel region is not limited to 5×5.

When there is a pixel having the same signal value as the target pixel in the eight peripheral pixels adjacent to the target pixel, the controller 150 specifies the pixel as an edge pixel. On the other hand, when there is no pixel having the same signal value as the target pixel in the eight peripheral pixels adjacent to the target pixel, the controller 150 cancels the initial setting of the target pixel, sets a new target pixel within the measurement pixel region, and then repeats the same operation as above. In FIG. 9A, pixels located on the lower left and upper right of the target pixel have the same signal value as the target pixel.

Next, the controller 150 repeats the same operation as above on eight peripheral pixels adjacent to the edge pixel set in the above to further specify a pixel having the same signal value as the target pixel. The controller 150 repeats the operation to specify edge pixels having the same signal value as the target pixel in the measurement pixel region (the 5×5 pixel region in FIG. 9A). In FIG. 9A, the pixels having the same signal value as the target pixel are shaded with slanted lines. In this manner, the target pixel and the edge pixel in the measurement pixel region are specified.

(Step S4a: Generation of Y-direction Differential Image)

Next, as illustrated in FIG. 9A, the controller 150 connects adjacent pixels in the target pixel and the edge pixels to each other by a vector (a dotted vector in FIG. 9A), and obtains a vector in a differential image generation direction (a vector indicated by a solid line in FIG. 9A) by flipping the dotted vector from top to bottom. The vector in the differential image generation direction is decomposed into the X direction and the Y direction as illustrated in FIG. 9B, and only a Y-direction component is extracted to generate a Y-direction differential image.

The Y-direction differential image generated in this manner is one obtained by vectorizing the Y component of edge information of the subject in the X-direction differential image and representing the vectorized Y component by a numerical value. The phase image generated using such a Y-direction differential image includes information about the Y-direction differential image, and thus has a higher accuracy than a phase image that is generated by processing only information about the X-direction differential image.

<Fourth Embodiment: Phase Image Processing Method>

The present embodiment is the same as the first embodiment except that, as illustrated in FIG. 2, a step (step S3b) of generating an intermediate phase image and a step (step S4b) of differentiating the intermediate phase image in the Y direction to generate a Y-direction differential image are included instead of steps S3 and S4 of the first embodiment. Hereinbelow, steps S3b and S4b which are modified from the first embodiment will be described. Since the other steps are the same as those of the first embodiment, description thereof will be omitted.

(Step S3b: Generation of Intermediate Phase Image)

Figure 10:
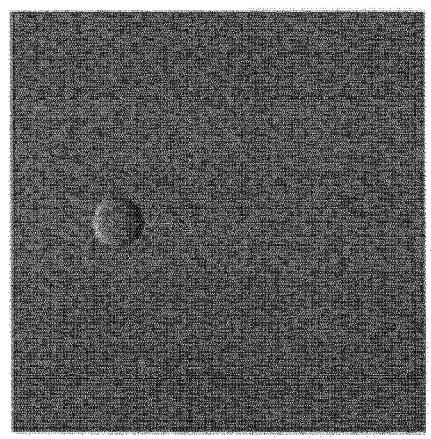
FIG. 10 is a sample of an X-direction differential image.
Figure 11:
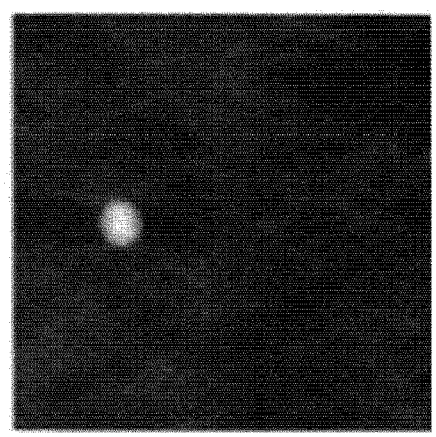
FIG. 11 is a sample of an intermediate phase image obtained by integrating the X-direction differential image in the X direction.

FIG. 10 is a sample of an X-direction differential image. FIG. 11 is a sample of an intermediate phase image obtained by integrating the X-direction differential image in the X direction. In step S3b, the intermediate phase image generator 155 integrates the X-direction differential image (FIG. 10) obtained in step S2 in the X direction to generate an intermediate phase image (FIG. 11). The integration in the X direction can be performed using the same method as the integration method in step S4 of the first embodiment.

(Generation of Intermediate Phase Image Using Fourier Transformation)

In the present embodiment, there has been described the case in which the X-direction differential image is integrated in the X direction to generate the intermediate phase image. Alternatively, the X-direction differential image may be further differentiated in the X direction to generate an X-direction secondary differential image, and the Poisson's equation may be applied to the X-direction secondary differential image to generate an intermediate phase image.

In this case, similarly to the application of the Poisson's equation in step S5 of the second embodiment, the Fourier transformation unit 159 performs a Fourier transformation on the X-direction secondary differential image to transform the secondary differential image to a frequency image. The integral operator application unit 160 applies a modified second-order integral operator to the frequency image to perform second-order integration to generate an operator applied frequency image. Then, the inverse Fourier transformation unit 161 performs an inverse Fourier transformation on the operator applied frequency image to generate an intermediate phase image.

The optimization operation unit 162 may perform an optimization operation on the intermediate phase image generated in the above. The optimization operation enables the accuracy of the intermediate phase image to be improved. In the optimization operation, a hypothesis that a difference (differential value) between signal values of pixels that are adjacent to each other in the X direction in the intermediate phase image is equal to a value of the X-direction differential value is set in an objective function in the X direction, and a hypothesis that signal values of pixels that are adjacent to each other in the Y direction are continuous with each other is set in an objective function in the Y direction. The X-direction objective function and the Y-direction objective function are performed by an operation represented by the following formula (18).

[Formula 18]

$$F(ph) = w1 \cdot \sum_{(u,v)} (\{ph(u, v) - ph(u-1, v)\} - dphX(u, v))^2 + w2 \cdot \sum_{(u,v)} (\{ph(u, v) - ph(u, v-1)\} - 0)^2 \quad (18)$$

In formula (18), F(ph) is an objective function in the optimization and indicates that the smaller a value of F (ph) is, the higher the accuracy of the intermediate phase image is. Further, ph(u, v) is a signal value of a pixel at coordinates (u, v) in the intermediate phase image which is a target of the optimization, and dphX(u, v) is a signal value of a pixel at coordinates (u, v) in the X-direction differential image.

The use of the intermediate phase image obtained by performing the optimization operation in this manner enables the phase image to have a higher accuracy. The optimization operation can be executed once or more. The accuracy of the phase image can be improved by increasing the number of times of performing the optimization operation. However, the optimization operation may not be performed.

(Step S4b: Generation of Y-direction Differential Image)

Figure 12:
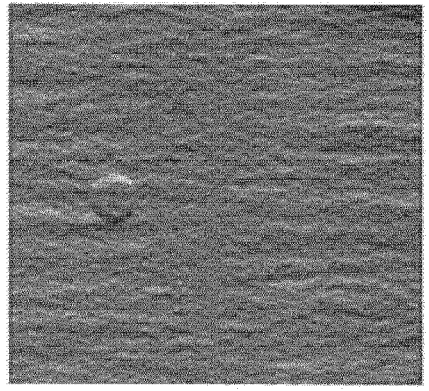
FIG. 12 is a sample of a Y-direction differential image obtained by differentiating the intermediate phase image in the Y direction.

Next, the second differential image generator 154 differentiates the intermediate phase image in the Y direction to generate a Y-direction differential image (S4b). FIG. 12 is a sample of the Y-direction differential image obtained by differentiating the intermediate phase image in the Y direction. The Y-direction differential image is calculated by the following formula (19). The Y-direction differentiation is performed by calculating a difference between a signal value of a pixel located at coordinates (u, v) in the intermediate phase image and a signal value of a pixel that is located at coordinates (u, v−1) and adjacent to this pixel on the negative side in the Y direction.

[Formula 19]

$$\frac{d(ph(u, v))}{dy} = ph(u, v) - ph(u, v-1) \quad (19)$$

The Y-direction differentiation is not limited to the one represented by formula (19), and may be performed by calculating a difference between a signal value of a pixel located at coordinates (u, v) in the intermediate phase image and a signal value of a pixel that is located at coordinates (u, v+1) and adjacent to this pixel on the positive side in the Y direction as represented by the following formula (20).

[Formula 20]

$$\frac{d(ph(u, v))}{dy} = ph(u, v+1) - ph(u, v) \quad (20)$$

The generation of a phase image using the Y-direction differential image generated in this manner enables the generation of the phase image including information about the Y-direction differential image. This enables the phase image to have a higher accuracy than a phase image generated using only the X-direction differential image.

<Fifth Embodiment: Phase Image Processing Method>

Figure 13:
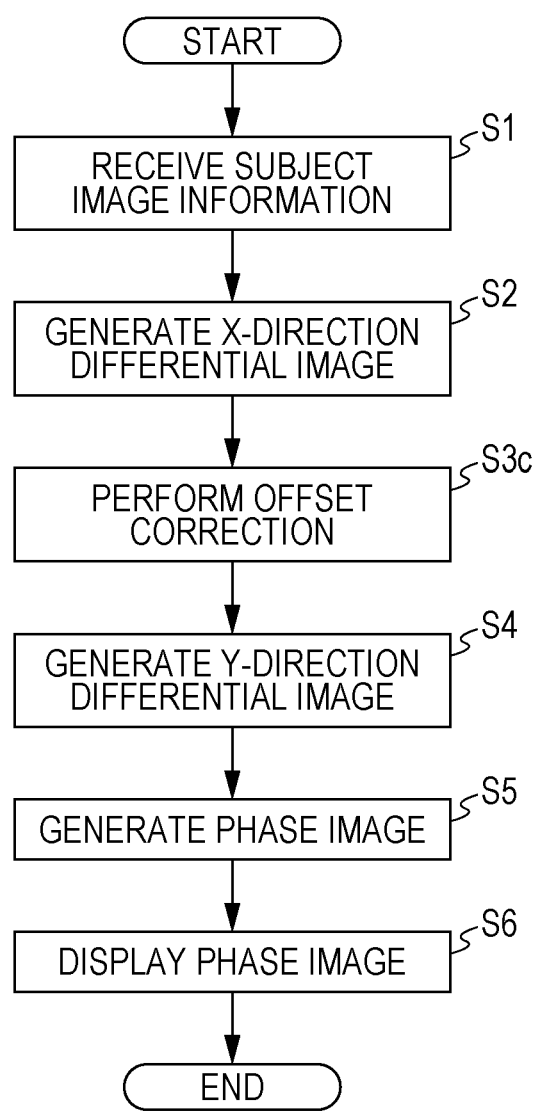
FIG. 13 is a flow chart illustrating a process of processing a phase image of a fifth embodiment.

FIG. 13 is a flow chart of a phase image processing method of the fifth embodiment. The present embodiment is the same as the first embodiment except that, as illustrated in FIG. 13, a step (step S3c) of offset-correcting a Y-direction error included in an X-direction differential image and a step (step S4c) of generating a Y-direction differential image on the basis of the corrected X-direction differential image are included instead of steps S3 and S4 of the first embodiment. Hereinbelow, steps S3c and S4c which are modified from the first embodiment will be described. Since the other steps are the same as those of the first embodiment, description thereof will be omitted.

(Step S3c: Offset Correction)

FIGS. 14A to 14D are schematic views for describing image processing of steps S3c and S4c. In step S3c, the controller 150 first sets a pixel region (for example, a 5×5 pixel region) that includes a part in which pixels each indicating an end (edge) of a subject are continuous with each other in the Y direction in the X-direction differential image obtained in step S2 of the first embodiment.

Figure 14A:
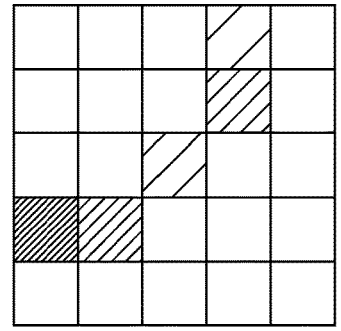
FIGS. 14A to 14D are schematic views for describing image processing for performing offset correction on an X-direction differential image.

FIG. 14A illustrates the pixel region that includes the part in which pixels each indicating the end (edge) of the subject are continuous with each other in the Y direction in the X-direction differential image. In the image illustrated in FIG. 14A, pixels shaded with slanted lines are pixels having signal values indicating the end of the subject. The difference in the signal values is indicated by the difference in the density of the slanted lines. In the X-direction differential image of FIG. 14A, the top two pixels in the fourth column from the left end are continuous with each other in the Y direction. Since the two pixels continuous in the Y direction indicate the end of the subject, the two pixels should originally have the same signal value. However, in the X-direction differential image in FIG. 14A, the Y-direction continuity is not ensured, and an error is included in the signal values of the Y-direction pixels. In order to correct the Y-direction error, the controller 150 performs the offset correction of step S3c.

Figure 14B:
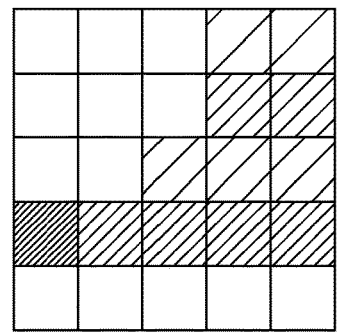
Figure 14C:
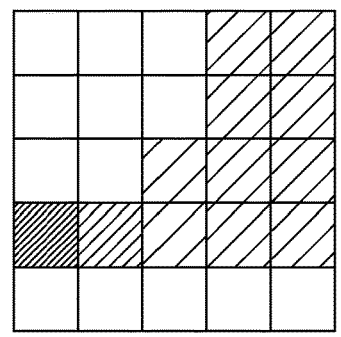

When the controller 150 simply integrates the X-direction differential image of FIG. 14A in the X direction, a signal value of each pixel is reflected to the positive side in the X direction as illustrated in FIG. 14B. The controller 150 performs offset correction in the Y direction on the pixel region of FIG. 14B. Accordingly, as illustrated in FIG. 14C, values of pixels continuous in the Y direction are corrected to the same value or approximate values. This enables the Y-direction error in the signal values of adjacent pixels to be reduced, which improves the accuracy of the Y-direction differential image.

(Step S4c: Generation of Y-direction Differential Image)

Figure 14D:
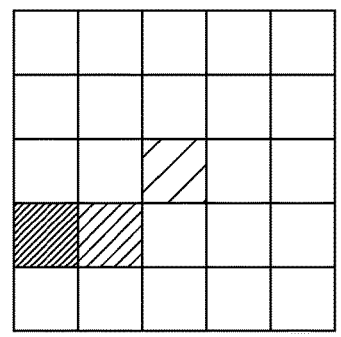

The second differential image generator 154 performs Y-direction differentiation on the offset-corrected pixel region to generate a Y-direction differential image (FIG. 14D). When the offset correction is performed in the above, two pixels continuous in the Y direction have the same signal value or approximate values. Thus, a differential value in the Y direction of the two pixels continuous in the Y direction is zero or almost zero. The accuracy of the Y-direction differential image can be improved by correcting an error in signal values of pixels continuous in the Y direction in this manner.

<Optimization Operation of Phase Image>

The optimization operation unit 162 may perform an optimization operation on the phase image generated in each of the above embodiments. The optimization operation enables the accuracy of the phase image to be improved. The optimization operation unit 162 can set a hypothesis that a difference (differential value) between signal values of pixels that are adjacent to each other in the X direction in the phase image is equal to a value of the X-direction differential image in an objective function in the X direction, and set a hypothesis that a difference (differential values) between signal values of pixels that are adjacent to each other in the Y direction in the phase image is equal to a value of the Y-direction differential image in an objective function in the Y direction. The X-direction objective function and the Y-direction objective function are performed by an operation represented by the following formula (21).

[Formula 21]

$$F(ph) = w1 \cdot \sum_{(u,v)} [\{ph(u, v) - ph(u - 1, v)\} - dphX(u, v)]^2 + \quad (21)$$
$$w2 \cdot \sum_{(u,v)} [\{ph(u, v) - ph(u, v - 1)\} - \{dphY(u, v)\}]^2$$

In formula (21), F(Ph) is an objective function in the optimization and indicates that the smaller a value of F (Ph) is, the higher the accuracy of the phase image is. Further, Ph(u, v) is a signal value of a pixel at coordinates (u, v) in the phase image which is a target of the optimization, dphX(u, v) is a signal value of a pixel at coordinates (u, v) in the X-direction differential image, and dphY(u, v) is a signal value of a pixel at coordinates (u, v) in the Y-direction differential image.

(First Modification of Optimization Operation)

The optimization operation unit 162 may multiply a weight (yweight(u, v)) which represents the continuity in the Y direction by a coefficient of the term of the Y-direction differential image in the above formula (21) to optimize the phase image. When the weight which represents the continuity in the Y direction is added, the optimization operation unit 162 performs an optimization operation represented by the following formula (22).

[Formula 22]

$$F(ph) = w1 \cdot \sum_{(u,v)} [\{ph(u, v) - ph(u - 1, v)\} - dphX(u, v)]^2 + \quad (22)$$
$$yweight(u, v) \times w2 \cdot \sum_{(u,v)} [\{ph(u, v) - ph(u, v - 1)\} - \{dphY(u, v)\}]^2$$

Incorporating the weight into formula (22) enables information about the difference between signal values of pixels in the Y direction to be incorporated into the Y-direction objective function. As a result, the accuracy of the phase image can be improved.

The weight representing the continuity in the Y direction is obtained, for example, by calculating a weight that represents the continuity between signal values of pixels that are adjacent to each other in the second direction using the X-direction differential image. The weight is calculated by the following formula (23). A method for calculating the weight representing the continuity in the Y direction is not limited to formula (23).

[Formula 23]

$$yweight(u, v) = \frac{\varepsilon}{\varepsilon + |dphX(u, v) - dphX(u, v - 1)|} \quad (23)$$

In the above formula (23), ε is a weight coefficient.

In the above formula (23), the weight representing the continuity in the Y direction varies according to the absolute value of the difference between signal values of pixels that are adjacent to each other in the Y direction in the X-direction differential image. The weight representing the continuity in the Y direction becomes larger as the difference between signal values of pixels that are adjacent to each other in the Y direction decreases. When pixels that are adjacent to each other in the Y direction have the same signal value, the weight representing the continuity in the Y direction becomes the maximum value, specifically, one. When the weight is used in the coefficient of Y-direction differential information in formula (22), it is possible to obtain a phase image in which a value having a higher certainty in the Y-direction differential image is more strongly reflected.

(Second Modification of Optimization Operation)

The optimization operation may be performed by changing the Y-direction objective function of the above optimization operation to a hypothesis that signal values of pixels that are adjacent to each other in the Y direction are continuous with each other. In this case, the X-direction objective function and the Y-direction objective function are performed by an operation represented by the following formula (24).

[Formula 24]

$$F(ph) = w1 \cdot \sum_{(u,v)} [\{ph(u, v) - ph(u-1, v)\} - dphX(u, v)]^2 + \quad (24)$$
$$w2 \cdot \sum_{(u,v)} [\{ph(u, v+1) - 2ph(u, v) + ph(u, v-1)\} - \{dphY(u, v+1) - dphY(u, v)\}]^2$$

(Modification)

In the description of each of the above embodiments, the direction perpendicular to the first direction (X direction) is defined as the second direction (Y direction). However, the X direction and the Y direction may not be perpendicular to each other, and it is only required that the X direction and the Y direction be different from each other.

The above first to fifth embodiments may be combined to generate a phase image. The phase image generated in each of the embodiments may be regarded as the intermediate phase image of the fourth embodiment, and a phase image may be again generated. Repeatedly performing the image processing in this manner enables the accuracy of the phase image to be improved.

<Sixth Embodiment: X-ray Imaging Apparatus>

The phase image processing method of the above embodiments can acquire, using a differential image in one direction (X direction), information about the difference between signal values of pixels that are arranged side by side in a direction (Y direction) different from the one direction. Thus, the phase image processing method of the above embodiments can be suitably used in an X-ray imaging apparatus which uses an X-ray Talbot interferometer or an X-ray Talbot-Lau interferometer which generates image information in one direction.

The X-ray imaging apparatus uses one of phase contrast methods which treat X-rays as waves and detect phase shift in the X-rays generated by passing through a subject to obtain a transmission image of the subject. The X-ray imaging apparatus has advantages such that an improvement in the sensitivity by approximately 1000 times compared to an absorption contrast method that obtains an image having contrast of the large/small of the X-ray absorption by a subject can be expected, and the X-ray irradiation amount can thereby be reduced to, for example, $\frac{1}{100}$ to $\frac{1}{1000}$. In the present embodiment, the X-ray imaging apparatus provided with an image controller that executes a program of executing the phase image processing method of each of the above embodiments will be described.

Figure 15:
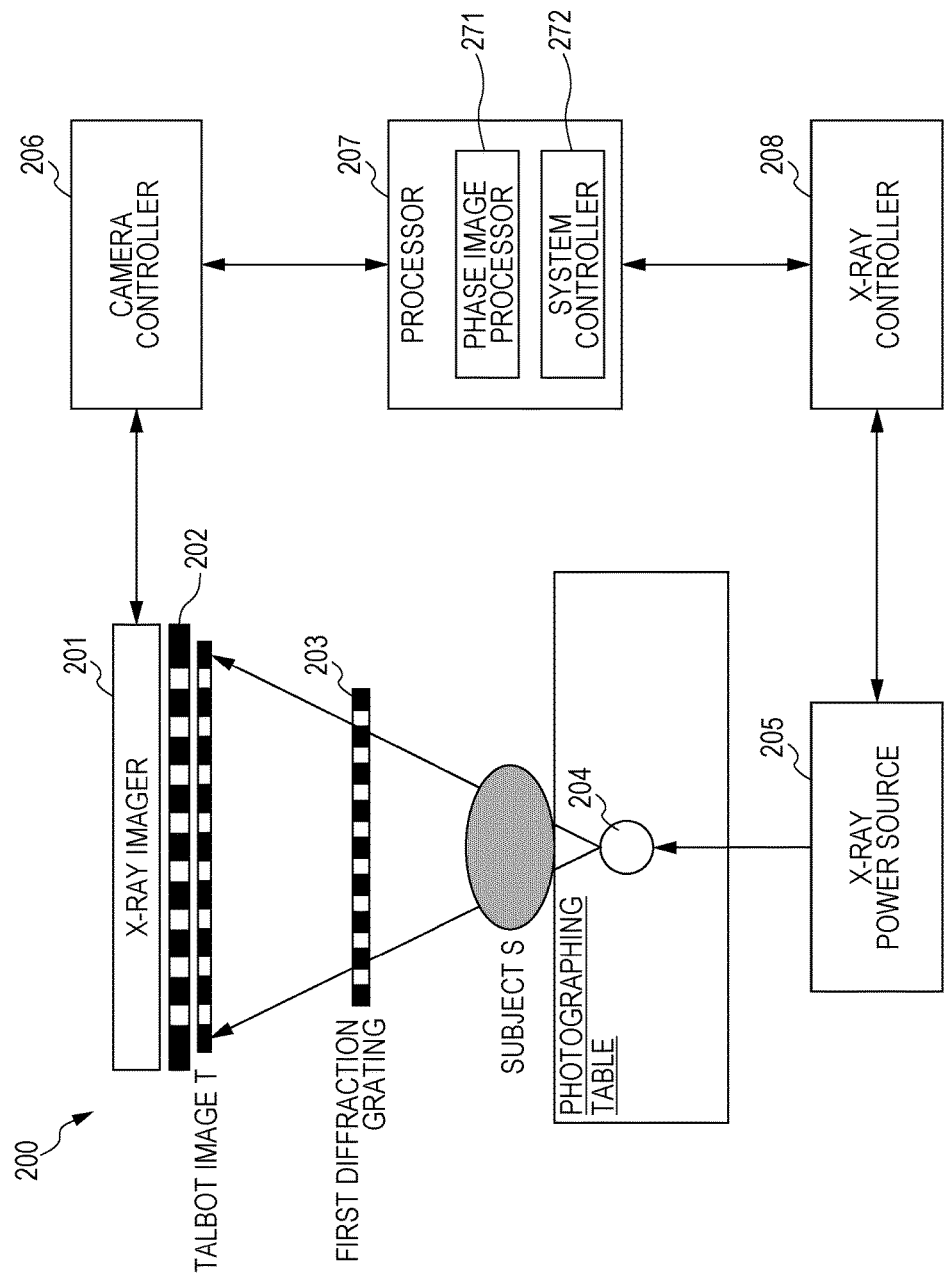
FIG. 15 is an explanatory diagram illustrating the configuration of an X-ray imaging apparatus in a sixth embodiment.

FIG. 15 is an explanatory diagram illustrating the configuration of the X-ray imaging apparatus in the sixth embodiment. In FIG. 15, the X-ray imaging apparatus 200 includes an X-ray imager 201, a second diffraction grating 202, a first diffraction grating 203, and an X-ray source 204. In the present embodiment, the X-ray imaging apparatus 200 further includes an X-ray power source 205 which supplies power to the X-ray source 204, a camera controller 206 which controls an imaging operation of the X-ray imager 201, a processor 207 which controls the entire operation of the X-ray imaging apparatus 200, and an X-ray controller 208 which controls a power supply operation of the X-ray power source 205 to control an X-ray radiation operation of the X-ray source 204.

The X-ray source 204 is a device that radiates X-rays in response to power supply from the X-ray power source 205 to apply the X-rays to the first diffraction grating 203. The X-ray source 204 is, for example, a device that radiates X-rays in such a manner that high voltage supplied from the X-ray power source 205 is applied between a cathode and an anode, and electrons released from a filament of the cathode collide against the anode to radiate X-rays.

The first diffraction grating 203 generates the Talbot effect by the X-rays radiated from the X-ray source 204. The first diffraction grating 203 is configured to satisfy conditions for generating the Talbot effect. The first diffraction grating 203 is a grating that is sufficiently coarser than the wavelength of the X-rays radiated from the X-ray source 204, for example, a phase type diffraction grating having a grating constant (diffraction grating frequency) d of approximately 20 times or more of the wavelength of the X-rays. The first diffraction grating 203 is a one-dimensional diffraction grating.

The second diffraction grating 202 is a transmission and amplitude type diffraction grating that is disposed at a position away from the first diffraction grating 203 by approximately a Talbot distance L and diffracts X-rays diffracted by the first diffraction grating 203. The second diffraction grating 202 is a one-dimensional diffraction grating.

These first and second diffraction gratings 203, 202 are set in conditions represented by the following formulae 1 and 2 for constructing a Talbot interferometer.

$$l = \lambda/(a/(L+Z1+Z2)) \quad \text{(Formula 1)}$$

$$Z1 = (m+1/2) \times (d^2/\lambda) \quad \text{(Formula 2)}$$

Here, l is a coherence length, $\lambda$ is a wavelength of an X-ray (generally, a center wavelength), a is an opening diameter of the X-ray source 204 in a direction substantially perpendicular to diffraction members of the diffraction gratings, L is a distance between the X-ray source 204 and the first diffraction grating 203, Z1 is a distance between the first diffraction grating 203 and the second diffraction grating 202, Z2 is a distance between the second diffraction grating 202 and an X-ray image detector 105, m is an integer, and d is a frequency of the diffraction members (the frequency of the diffraction grating, the grating constant, a distance between the centers of adjacent diffraction members, the pitch P).

The X-ray imager 201 is a device that captures an image of X-rays diffracted by the second diffraction grating 202. The X-ray imager 201 includes, for example, a flat panel detector (FPD) provided with a two-dimensional image sensor including a thin film layer formed on a light receiving surface, the thin film layer including a scintillator which absorbs the energy of X-rays and emits fluorescence or an image intensifier camera provided with an image intensifier unit which converts incident photons into electrons on a photoelectric surface, doubles the electrons by a microchannel plate, and allows a group of the doubled electrons to collide against a phosphor to emit light and a two-dimensional image sensor which images the light output from the image intensifier unit.

The processor 207 is a device that controls each unit of the X-ray imaging apparatus 200 to control the entire operation of the X-ray imaging apparatus 200. The processor 207, for example, includes a microprocessor and a peripheral circuit thereof, and functionally includes a phase image processor 271 and a system controller 272.

The system controller 272 performs transmission and reception of a control signal with the X-ray controller 208 to control an X-ray radiation operation in the X-ray source 204 through the X-ray power source 205, and performs transmission and reception of a control signal with the camera controller 206 to control an imaging operation of the X-ray imager 201. X-rays are applied toward a subject S by the control of the system controller 272. An image generated by the application of the X-rays is captured by the X-ray imager 201, and an image signal is input to the processor 207 through the camera controller 206.

The phase image processor 271 processes the image signal generated by the X-ray imager 201 to generate a phase image of the subject S. The phase image processor 271 functionally includes the first differential image generator 151, the phase image generator 152, the secondary differential image generator 153, and the second differential image generator 154 describe above. The phase image processing methods of the first to fifth embodiments or a combination of these methods are used as processing performed by the phase image processor 271. The use of such phase image processing enables a phase image having a high accuracy to be obtained.

Next, the operation of the X-ray imaging apparatus of the present embodiment will be described. When the subject S is mounted on, for example, a photographing table which is provided with the X-ray source 204 inside (on the back face) thereof, the subject S is placed between the X-ray source 204 and the first diffraction grating 203. When a user (operator) of the X-ray imaging apparatus 200 instructs imaging of the subject S from an operation unit (not illustrated), the system controller 272 of the processor 207 outputs a control signal to the X-ray controller 208 to apply X-rays toward the subject S. In response to the control signal, the X-ray controller 208 controls the X-ray power source 205 to supply power to the X-ray source 204. The X-ray source 204 radiates X-rays to apply the X-rays to the subject S.

The applied X-rays pass through the first diffraction grating 203 through the subject S so as to be diffracted by the first diffraction grating 203, so that a Talbot image T which is a self-image of the first diffraction grating 203 is formed at a position away therefrom by the Talbot distance L (=Z1). The second diffraction grating 202 which has a frequency corresponding to the first diffraction grating 203 is disposed at the position where the self-image is formed. When the second diffraction grating 202 is displaced by a predetermined amount in a direction (the direction corresponding to the "first direction", or the "X direction" in the phase image processing) that is perpendicular to an extending direction of a slit of the second diffraction grating 202 with the distance from the first diffraction grating 203 maintained, a moire image having a fringe pattern reflecting distortion caused by the transmittance of the subject S is generated. The moire fringe image is captured by the X-ray imager 201, for example, whose exposure time is controlled by the system controller 272.

The X-ray imager 201 outputs an image signal of the moire fringe image to the processor 207 through the camera controller 206. The image signal is processed by the phase image processor 271 of the processor 207.

Since the subject S is placed between the X-way source 204 and the first diffraction grating 203, an X-ray that has passed through the subject S is shifted in phase with respect to an X-ray that has not passed through the subject S. Thus, the X-ray incident on the first diffraction grating 203 includes torsion on the wave surface thereof, and deformation corresponding to the torsion is generated in the Talbot image T. Thus, moire fringes of an image generated by the superimposition between the Talbot image T and the second diffraction grating 202 is modulated by the subject S. The amount of the modulation is proportional to a bent angle of the X-ray bent by a refractive effect by the subject S. Thus, the structure of the subject S and the inside thereof can be detected by analyzing the moire fringes. Further, a tomographic image of the subject S can be formed by X-ray phase computed tomography (CT) by imaging the subject from a plurality of angles.

In the X-ray imaging apparatus 200 described above, the X-ray source 204, the first diffraction grating 203, and the second diffraction grating 202 constitute a Talbot interferometer. Alternatively, an X-ray metal gating as a multislit may further be disposed on the X-ray radiation side of the X-ray source 204 to constitute a Talbot-Lau interferometer. Such a Talbot-Lau interferometer enables the amount of X-rays applied to the subject S to be increased compared to a single slit. As a result, more excellent moire fringes can be obtained, and an image of the subject S having a higher accuracy can be obtained.

In the X-ray imaging apparatus 200 described above, the subject S is placed between the X-ray source 204 and the first diffraction grating 203. Alternatively, the subject S may be placed between the first diffraction grating 203 and the second diffraction grating 202. In the X-ray imaging apparatus 200, an image of X-rays is captured by the X-ray imager 201 to obtain electronic data of the image. Alternatively, an image of X-rays may be captured by an X-ray film.

The embodiments described above include the following invention.

An image processing method includes a step of generating a differential image in a first direction on the basis of image information of a subject and a step of generating a phase image on the basis of the first-direction differential image and information about a difference between signal values of pixels arranged side by side in a second direction different from the first direction in the first-direction differential image.

In a conventional method, signal values of pixels of a differential image are integrated in the first direction (X direction) to generate a phase image. However, the differential image includes only differential information in the first direction, and includes no differential information in a direction other than the X direction. Thus, when a phase image is calculated on the basis of the differential image, many false images are included.

The phase image processing method takes into consideration information about the difference between signal values of pixels arranged side by side in the second direction in the differential image to generate a phase image. Thus, it is possible to generate a phase image having a higher accuracy than a phase image that is generated using only information about a differential image in one direction.

The phase image processing method preferably further includes a step of differentiating the first-direction differential image in the second direction to generate a secondary differential image and a step of integrating the secondary differential image in the first direction to generate a differential image in the second direction. The step of generating the phase image preferably generates the phase image on the basis of the first-direction differential image and the second-direction differential image.

The second-direction differential image included in the first-direction differential image can be acquired by differentiating the first-direction differential image in the second direction as described above. When the second-direction differential image is used together with the first-direction differential image to generate the phase image, the phase image having information in the second direction can be generated. Thus, the accuracy of the phase image can be improved.

The phase image processing method preferably further includes a step of integrating the first-direction differential image in the first direction to generate an intermediate phase image and a step of differentiating the intermediate phase image in the second direction to generate a differential image in the second direction. The step of generating the phase image preferably generates the phase image on the basis of the first-direction differential image and the second-direction differential image.

In this manner, the first-direction differential image may be integrated in the first direction to generate the intermediate phase image. The intermediate phase image may be differentiated in the second direction to generate the second-direction differential image.

The phase image processing method preferably further includes a step of specifying pixels each having a signal value indicating an end of the subject in the first-direction differential image and a step of decomposing a vector connecting the specified pixels into the first direction and the second direction to generate a differential image in the second direction. The step of generating the phase image preferably generates the phase image on the basis of the first-direction differential image and the second-direction differential image.

The end of the subject may be specified on the basis of pixels on the end of the subject in the first-direction differential image, and a second-direction component of a vector connecting the pixels may be extracted to acquire a differential image in the second direction.

The phase image processing method preferably further includes a step of further differentiating the first-direction differential image in the first direction to generate a first-direction secondary differential image, a step of further differentiating the second-direction differential image in the second direction to generate a second-direction secondary differential image, a step of performing a Fourier transformation on a composite image generated by adding the first-direction secondary differential image and the second-direction differential image to generate a frequency image, and a step of performing an inverse Fourier transformation on an integral operator applied frequency image generated by applying an integral operator to the frequency image to generate the phase image.

When the frequency image is generated on the basis of the first-direction secondary differential image and the second-direction secondary differential image using the Fourier transformation and a phase image is then generated by the inverse Fourier transformation, not only the first-direction secondary differential image, but also the second-direction secondary differential image is used. Thus, a phase image having a high accuracy that includes the second-direction image information can be generated.

The phase image processing method preferably further includes a step of performing an optimization operation on a signal value of each pixel in the phase image using an objective function that includes a term of the second-direction differential image.

The optimization operation on the phase image enables the accuracy of the phase image to be improved.

The phase image processing method preferably further includes a step of calculating a weight representing continuity between signal values of pixels arranged adjacent to each other in the second direction on the basis of the second-direction differential image. The optimization operation is preferably performed using the calculated weight in a coefficient of the term of the second-direction differential image in the objective function in the step of performing the optimization operation.

The use of the weight calculated in this manner in the coefficient of the term of the second-direction differential image enables a part in which signal values of pixels are continuous with each other in the second-direction differential image to be easily extracted. As a result, a phase image having a high accuracy can be obtained.

An image processing apparatus includes a first-direction differential image generator which generates a differential image in a first direction on the basis of image information of a subject and a phase image generator which generates a phase image on the basis of the first-direction differential image and information about a difference between signal values of pixels arranged side by side in a second direction different from the first direction in the first-direction differential image.

The generation of a phase image using not only the first-direction differential image, but also the information about the difference between signal values of pixels arranged side by side in the second direction in the above manner enables the generation of the phase image having a higher accuracy than a phase image that is generated depending only on information about a differential image in one direction.

An image processing apparatus includes a first differential image generator which generates a differential image in a first direction of a subject on the basis of a Talbot image obtained by moving a one-dimensional grating included in a Talbot interferometer or a Talbot-Lau interferometer by a predetermined amount in the first direction and a phase image generator which generates a phase image on the basis of the first-direction differential image and information about a difference between signal values of pixels arranged side by side in a second direction different from the first direction in the first-direction differential image.

The Talbot image is two-dimensional image data obtained by moving the one-dimensional grating by a predetermined amount in the first direction. Thus, the Talbot image includes only information about the difference between signal values of pixels in the first direction. The use of the information about the difference between signal values of pixels arranged side by side in the second direction in the first-direction differential image using the Talbot image enables the generation of a phase image having a high accuracy.

A non-transitory computer-readable recording medium stores an image processing program for causing a computer that functions as an image display device provided with an input unit, an output unit, and a control processor to execute a step of generating a differential image in a first direction on the basis of image information of a subject and a step of generating a phase image on the basis of the first-direction differential image and information about a difference between signal values of pixels arranged side by side in a second direction different from the first direction in the first-direction differential image.

The image processing program stored in the recording medium generates a phase image using the information about the difference between signal values of pixels arranged side by side in the second direction in the first-direction differential image. Thus, it is possible to generate a phase image having a higher accuracy than a phase image that is generated depending only on information about the first-direction differential image.

According to an embodiment of the present invention, it is possible to provide an image processing method and an image processing apparatus that generate a phase image having a high accuracy in a simplified manner, an X-ray imaging apparatus that uses the image processing apparatus, and an image processing program for causing a computer to execute the image processing method.

Although the present invention has been described and illustrated in detail, it is clearly understood that the same is by way of illustrated and example only and is not to be taken by way of limitation, the scope of the present invention being interpreted by terms of the appended claims.

What is claimed is:

1. An image processing method for generating a phase image, the image processing method comprising
   generating a phase image on the basis of a differential image in a first direction based on image information of a subject and a differential image in a second direction different from the first direction, the second-direction differential image including information about a difference between signal values of pixels arranged side by side in the second direction in the first-direction differential image,
   wherein the image information has been generated with x-rays,
   wherein the second-direction differential image is generated based on said first-direction differential image, and
   wherein the pixels in the first-direction differential image are pixels arranged adjacent to each other in the second direction.

2. The image processing method according to claim 1, wherein the generating step comprises:
   differentiating the first-direction differential image in the second direction to generate a secondary differential image; and
   integrating the secondary differential image in the first direction to generate the second-direction differential image.

3. The image processing method according to claim 2, wherein the generating step comprises:
   differentiating the first-direction differential image in the first direction to generate a first-direction secondary differential image;
   differentiating the second-direction differential image in the second direction to generate a second-direction secondary differential image;
   performing a Fourier transformation on a composite image generated by adding the first-direction secondary differential image and the second-direction secondary differential image to generate a frequency image; and
   performing an inverse Fourier transformation on an integral operator applied frequency image generated by applying an integral operator to the frequency image to generate the phase image.

4. The image processing method according to claim 2, wherein the generating step comprises:
   performing an optimization operation on a signal value of each pixel in the phase image using an objective function including a term of the second-direction differential image.

5. The image processing method according to claim 4, wherein the generating step comprises:
   calculating a weight representing continuity between signal values of pixels arranged adjacent to each other in the second direction on the basis of the first-direction differential image, wherein
   the optimization operation is performed using the calculated weight in a coefficient of the term of the second-direction differential image in the objective function in the step of performing the optimization operation.

6. The image processing method according to claim 1, wherein the generating step comprises:
   integrating the first-direction differential image in the first direction to generate an intermediate phase image; and
   differentiating the intermediate phase image in the second direction to generate the second-direction differential image.

7. The image processing method according to claim 1, wherein the generating step comprises:
   specifying pixels each having a signal value indicating an end of the subject in the first-direction differential image; and
   decomposing a vector connecting the specified pixels into the first direction and the second direction to generate the second-direction differential image.

8. An image processing apparatus comprising a control processor for image processing, the control processor comprising
   a phase image generator configured to generate a phase image on the basis of a differential image in a first direction based on image information of a subject and a differential image in a second direction different from the first direction, the second-direction differential image including information about a difference between signal values of pixels arranged side by side in the second direction in the first-direction differential image,
   wherein the image information has been generated with x-rays,
   wherein the second-direction differential image is generated based on said first-direction differential image, and
   wherein the pixels in the first-direction differential image are pixels arranged adjacent to each other in the second direction.

9. The image processing apparatus according to claim 8, wherein the control processor further comprises:
   a differential image generator configured to differentiate the first-direction differential image in the second direction to generate a secondary differential image; and a differential image generator configured to integrate the secondary differential image in the first direction to generate the second-direction differential image.

10. The image processing apparatus according to claim 9, wherein the control processor further comprises:
   a first-direction secondary differential image generator configured to differentiate the first-direction differential image in the first direction to generate a first-direction secondary differential image;
   a second-direction secondary differential image generator configured to differentiate the second-direction differential image in the second direction to generate a second-direction secondary differential image;
   a Fourier transformation unit configured to perform a Fourier transformation on a composite image generated by adding the first-direction secondary differential image and the second-direction secondary differential image to generate a frequency image; and
   an inverse Fourier transformation unit configured to perform an inverse Fourier transformation on an integral operator applied frequency image generated by applying an integral operator to the frequency image to generate the phase image.

11. The image processing apparatus according to claim 9, wherein the control processor further comprises an optimization operation unit configured to perform an optimization operation on a signal value of each pixel in the phase image using an objective function including a term of the second-direction differential image.

12. The image processing apparatus according to claim 11, wherein the control processor further comprises:
   a weight operation unit configured to calculate a weight representing continuity between signal values of pixels arranged adjacent to each other in the second direction on the basis of the first-direction differential image, wherein
   the optimization operation unit performs the optimization operation using the calculated weight in a coefficient of the term of the second-direction differential image in the objective function.

13. The image processing apparatus according to claim 8, wherein the control processor further comprises:
   an intermediate phase image generator configured to integrate the first-direction differential image in the first direction to generate an intermediate phase image; and
   a differential image generator configured to differentiate the intermediate phase image in the second direction to generate the second-direction differential image.

14. The image processing apparatus according to claim 8, wherein the control processor further comprises: a controller configured to specify pixels each having a signal value indicating an end of the subject in the first-direction differential image, wherein the controller decomposes a vector connecting the specified pixels into the first direction and the second direction to generate the second-direction differential image.

15. The image processing apparatus according to claim 8, wherein the control processor further comprises a first differential image generator configured to generate the first-direction differential image on the basis of a Talbot image obtained by moving a one-dimensional grating included in a Talbot interferometer or a Talbot-Lau interferometer by a predetermined amount in the first direction.

16. An X-ray imaging apparatus comprising:
   a light source configured to radiate X-rays;
   a Talbot interferometer or a Talbot-Lau interferometer including a one-dimensional grating;
   an imager configured to capture a moire image formed by the Talbot interferometer or the Talbot-Lau interferometer, the moire image including information about a subject by the X-rays; and
   an image processing apparatus configured to image-process the moire image, the image processing apparatus comprising a phase image generator configured to generate a phase image on the basis of a differential image in a first direction based on the moire image and a differential image in a second direction different from the first direction, the second-direction differential image including information about a difference between signal values of pixels arranged side by side in the second direction in the first-direction differential image,
   wherein the second-direction differential image is generated based on said first-direction differential image, and
   wherein the pixels in the first-direction differential image are pixels arranged adjacent to each other in the second direction.

17. A non-transitory computer-readable recording medium storing a program for causing a computer to execute an image processing method, the image processing method comprising
   generating a phase image on the basis of a differential image in a first direction based on image information of a subject and a differential image in a second direction different from the first direction, the second-direction differential image including information about a difference between signal values of pixels arranged side by side in the second direction different from the first direction in the first-direction differential image,
   wherein the image information has been generated with x-rays,
   wherein the second-direction differential image is generated based on said first-direction differential image, and
   wherein the pixels in the first-direction differential image are pixels arranged adjacent to each other in the second direction.

* * * * *